(12) United States Patent
Takahashi (10) Patent No.: US 11,389,136 B2
(45) Date of Patent: Jul. 19, 2022

(54) ULTRASONIC PROBE

(71) Applicant: Hitachi, Ltd., Tokyo (JP)

(72) Inventor: Tomoo Takahashi, Tokyo (JP)

(73) Assignee: FUJIFILM HEALTHCARE CORPORATION, Kashiwa (JP)

( * ) Notice: Subject to any disclaimer, the term of this patent is extended or adjusted under 35 U.S.C. 154(b) by 151 days.

(21) Appl. No.: 16/639,263

(22) PCT Filed: May 8, 2018

(86) PCT No.: PCT/JP2018/017743
§ 371 (c)(1),
(2) Date: Feb. 14, 2020

(87) PCT Pub. No.: WO2019/044039
PCT Pub. Date: Mar. 7, 2019

(65) Prior Publication Data
US 2020/0245972 A1      Aug. 6, 2020

(30) Foreign Application Priority Data

Aug. 28, 2017 (JP) .............................. JP2017-162964

(51) Int. Cl.
*A61B 8/00* (2006.01)
*A61B 8/12* (2006.01)

(52) U.S. Cl.
CPC .............. *A61B 8/4461* (2013.01); *A61B 8/12* (2013.01); *A61B 8/4455* (2013.01)

(58) Field of Classification Search
None
See application file for complete search history.

(56) References Cited

U.S. PATENT DOCUMENTS

| | | | |
|---|---|---|---|
| 5,085,221 A * | 2/1992 | Ingebrigtsen | A61B 1/267 600/446 |
| 5,090,414 A | 2/1992 | Takano | |
| 6,063,035 A * | 5/2000 | Sakamoto | A61B 8/12 600/462 |
| 2015/0065887 A1* | 3/2015 | Park | A61B 8/4455 600/466 |
| 2016/0120505 A1* | 5/2016 | Kadokura | A61B 8/4461 600/462 |

(Continued)

FOREIGN PATENT DOCUMENTS

| | | |
|---|---|---|
| JP | S62-152441 A | 7/1987 |
| JP | H1-157713 U | 10/1989 |

(Continued)

OTHER PUBLICATIONS

International Preliminary Report on Patentability issued in corresponding International Application No. PCT/JP2018/017743 dated Mar. 12, 2020 including Forms PCT/IB/326 and PCT/IB/338.

(Continued)

*Primary Examiner* — Shahdeep Mohammed
(74) *Attorney, Agent, or Firm* — Foley & Lardner LLP (57) ABSTRACT

An ultrasonic probe includes a tip part, an operation part and a middle part. A motor is disposed in a cantilever system in a front portion in the middle part. The motor extends in a direction of a central axis of a shaft-like part. A driving force generated by the motor is transferred to a scanning mechanism. A vibrator part vibrates by the scanning mechanism.

6 Claims, 10 Drawing Sheets

(56) References Cited

U.S. PATENT DOCUMENTS

2016/0183914 A1\* 6/2016 Fujimura ................ A61B 8/12
600/459
2017/0290565 A1 10/2017 Fujii et al.

FOREIGN PATENT DOCUMENTS

| | | |
|---|---|---|
| JP | H2-55050 A | 2/1990 |
| JP | H2-167150 A | 6/1990 |
| JP | H3-151942 A | 6/1991 |
| JP | H03-289950 A | 12/1991 |
| JP | 2000-333960 A | 12/2000 |
| JP | 2005-168614 A | 6/2005 |
| JP | 2007-37564 A | 2/2007 |
| JP | 2016-087056 A | 5/2016 |
| JP | 2017-189610 A | 10/2017 |

OTHER PUBLICATIONS

Office Action issued in corresponding Japanese Patent Application No. 2017-162964 dated Jul. 7, 2020, with machine translation.
International Search Report with English translation and Written Opinion issued in corresponding application No. PCT/JP2018/017743 dated Jul. 3, 2018.

\* cited by examiner

ULTRASONIC PROBE

TECHNICAL FIELD

The present invention relates to an ultrasonic probe, and particularly to an ultrasonic probe of a body cavity insertion type.

BACKGROUND ART

Ultrasonic diagnosis apparatus are utilized in medical fields. The ultrasonic diagnosis apparatus is generally configured by an apparatus body and an ultrasonic probe. As the ultrasonic probe, there are known a body surface contacting type probe and a body cavity insertion type probe. As an example of the latter, there are a transvaginal probe, a transrectal probe, and a transesophageal probe. In a case where volume data (three-dimensional data) is acquired in the body cavity, for example, a mechanical scanning type 3D-probe is used.

The mechanical scanning type 3D-probe includes a tip part which stores a vibrator unit and a scanning mechanism, a middle part which extends from the tip part, and an operation part which is connected to the middle part. The tip part and the middle part form an insertion part. The insertion part is inserted in the body cavity. The tip part is normally filled with an acoustic medium. In order to mechanically scan the vibrator unit in the acoustic medium, there is a need to provide the driving source which generates a corresponding driving force in the 3D probe.

PTLs 1 to 3 disclose the ultrasonic probe. In the ultrasonic probe, a motor is disposed in a grip having a relatively large margin in space. The driving force generated by the motor is transferred to the scanning mechanism in the tip part through a driving force transfer member such as a shaft which passes through the middle part. PTLs 1 to 3 fail to disclose a detail structure in the tip part, especially a detail structure of a vibrator part.

CITATION LIST

Patent Literature

PTL 1: JP 2-167150 A
PTL 2: JP 2-55050 A
PTL 3: JP 2005-168614 A

SUMMARY OF INVENTION

Technical Problem

In a case where the driving source is provided in the operation part in the mechanically scanning type ultrasonic probe which includes the tip part inserted in the body cavity, a driving force transfer member having a considerably long length is required to be disposed in the middle part, and the ultrasonic probe is made heavy by that amount. In addition, the shape of the operation part is restricted. Further, there is little space margin in the tip part, and further miniaturization is required.

An object of the invention is to reduce the weight of a mechanically scanning ultrasonic probe which includes the tip part inserted in the body cavity. Alternatively, an object of the invention is to bring the driving source near to the scanning mechanism.

Solution to Problem

An ultrasonic probe according to the invention includes a tip part which is inserted in a body cavity and stores a vibrator part and a scanning mechanism which mechanically scans the vibrator part, an operation part which is gripped by a user, and a middle part which is provided between the tip part and the operation part, and stores a driving source which generates a driving force to be transferred to the scanning mechanism.

DESCRIPTION OF EMBODIMENTS (1) Outline of Embodiment

An ultrasonic probe according to an embodiment includes a tip part, an operation part, and a middle part. The tip part is a portion which is inserted into a body cavity, and a portion which stores a vibrator part and a scanning mechanism which mechanically scans the vibrator part. The operation part is a portion which is gripped by a user. The middle part is a portion provided between the tip part and the operation part, and a portion which stores a driving source to generate a driving force transferred to the scanning mechanism.

According to the above configuration, the driving source is provided in the middle part. Therefore, a driving force transfer mechanism from the driving source to the scanning mechanism can be made small or simply, so that the ultrasonic probe can be reduced in weight. In addition, there is no need to provide the driving source in the operation part. Therefore, the operation part can be shaped to some degree of freedom. There is no need to make the portions of the middle part and the operation part straight in order to transfer the driving force. The vibrator part includes at least one vibration element which transmits and receives an ultrasonic wave. In the embodiment, a plurality of vibration elements are provided. The user is a doctor, an inspection engineer, or the like.

In the embodiment, the middle part includes a front portion connected to the tip part. The driving source is disposed inside the front portion. With this configuration, the driving source can be brought near to the scanning mechanism, and the ultrasonic probe can be still reduced in weight. Further, the driving source may be disposed inside a center portion or a back portion of the middle part for a weight balance or other reasons.

In the embodiment, a tip portion of the driving source is held in a cantilever system by a holding member which is disposed inside the tip part or the middle part. With this configuration, the number of components can be reduced compared to a case where a both end support system is employed. In addition, there is no need to provide complex structures in the middle part. Further, from the viewpoint of vibration suppression and secure holding, a plurality of places in a longitudinal direction in the driving source may be held by a plurality of holding members.

In the embodiment, the middle part includes a shaft-like part and a neck part which is connected to the shaft-like part. The tip part is made thickener than the shaft-like part. The neck part has a shape gradually thickening from the shaft-like part to the tip part. The holding member is disposed inside the neck part. Since the neck part tends to have space, the holding member is disposed in the inner space thereof. The tip portion of the driving source may be held by a structure in the tip part.

In the embodiment, the shaft-like part includes a first central axis. The driving source is disposed on the first central axis in the middle part. The driving source has an elongating shape along the first central axis. With this configuration, the weight balance can be favorably kept. In addition, the inner space of the middle part can be utilized. If an elongating motor is used as a driving source, the outer diameter of the shaft-like part can be made small.

In the embodiment, the tip part includes a second central axis which is in parallel with the first central axis and is provided at a position shifted from the first central axis. A central point in an electronic scanning direction and a central point in a mechanically scanning direction are on the second central axis. This configuration is considered on an assumption that the tip part becomes thickened in a shift direction from the first central axis to the second central axis. If the thickening of the tip part is suppressed in a direction opposite the shift direction, even if a puncture needle is disposed in a state close to the shaft-like part, the puncture needle hardly abuts on the tip part.

In the embodiment, the middle part includes a hollow resin case and a metal pipe which is disposed in the resin case and is connected to the holding member while storing the driving source. The metal pipe forms a frame of the middle part. In other words, the rigidity of the middle part is increased by the metal pipe. With the metal pipe, it can also be expected that electromagnetic noises from the outside are suppressed. The metal pipe may be indirectly connected to the structure in the tip part through the holding member. According to such a configuration, the connection portion between the tip part and the middle part can be reinforced in structure.

In the embodiment, the middle part includes a ring-like gap formed around the driving source, and a wiring member drawn out of the vibrator part passes through the ring-like gap and extends up to the operation part. The wiring member may be configured as a laminated body of a plurality of wiring sheets, and the laminated body passes through the gap. Alternatively, the wiring member may be configured to pass through the gap in a state where the plurality of wiring sheets are dispersed.

In the embodiment, the wiring member includes at least one wiring sheet equipped with a signal line array. The wiring sheet includes a driving source proximity portion as a portion which passes through the ring-like gap. At least the driving source proximity portion in the wiring sheet includes a first ground surface electrode provided on one side of the signal line array and a second ground surface provided on the other side of the signal line array.

With this configuration, the signal line array is interposed by a pair of ground surface electrodes. Therefore, the entering of the electromagnetic noises from the driving source to the signal line array is suppressed. A reduction of electrical crosstalk between the signal lines is also expected. The above configuration may be employed to the entire middle part. In a case where the configuration of a plurality of wiring sheets drawing out of the vibrator part is employed in the tip part, the load of the mechanical scanning of the vibrator part is reduced. Therefore, the wiring sheet may be reduced in weight. For example, only one side of the signal line array may be provided with the ground surface electrode.

(2) Details of Embodiment

Figure 1:
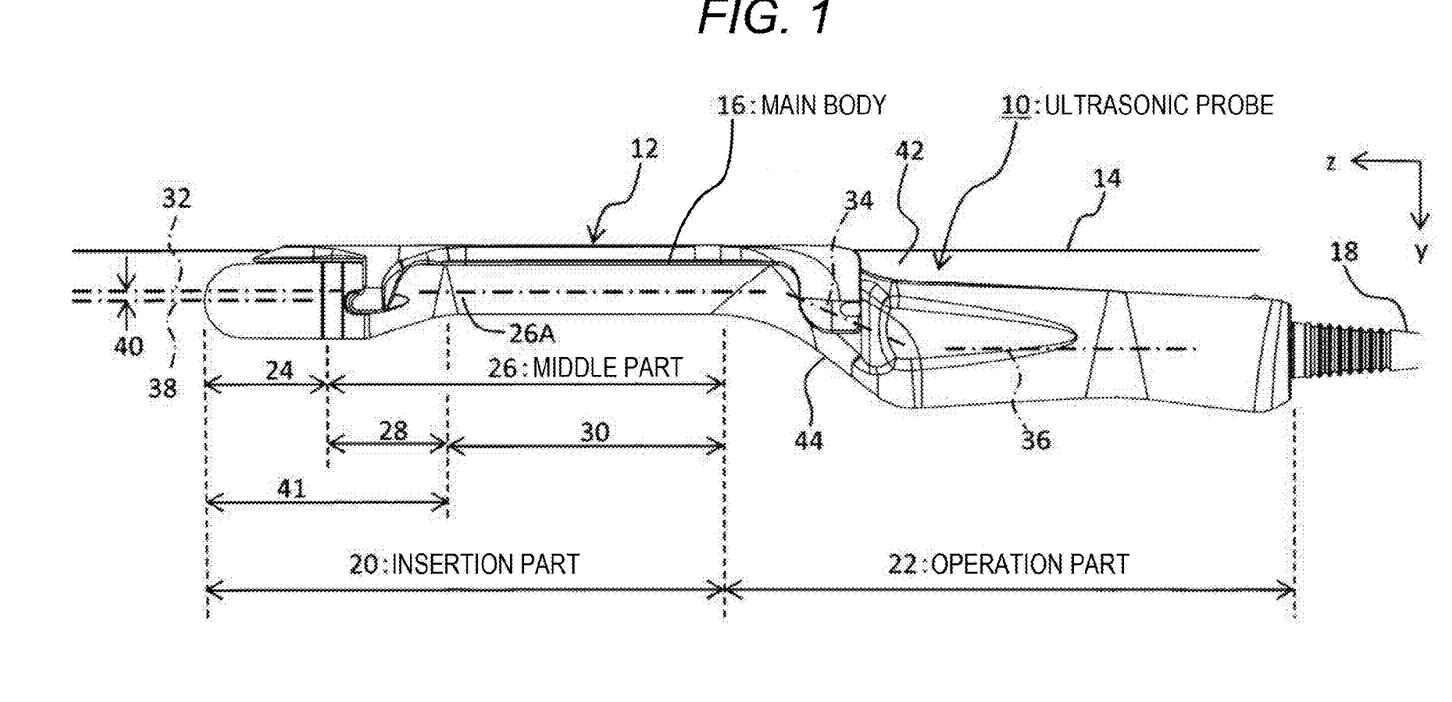
FIG. 1 is a side view illustrating an ultrasonic probe according to an embodiment.

FIG. 1 illustrates an ultrasonic probe 10 according to the embodiment. The ultrasonic probe 10 is a 3D probe of a body cavity insertion type and a mechanically scanning type. Examples of the body cavity include a vagina, a rectum, and an esophagus. In an exemplary configuration illustrated in FIG. 1, a puncture adapter 12 is mounted in the ultrasonic probe 10. The puncture adapter 12 is a tool to hold and guide a puncture needle 14. In a case where the puncturing is performed, the puncture adapter 12 is mounted in the ultrasonic probe 10. In a case where the puncturing is not performed, the puncture adapter 12 is taken away from the ultrasonic probe 10.

The ultrasonic probe 10 includes a main body 16, a cable 18, and a connector (not illustrated). The connector of the ultrasonic probe 10 is physically and electrically connected to a connector of a main body of an ultrasonic diagnosis apparatus (not illustrated). The main body 16 is roughly configured by an insertion part 20 and an operation part 22. The insertion part 20 is a portion which can be inserted into the body cavity. The insertion part 20 has a shape extending in a z direction which is an insertion direction. The operation part 22 is a portion which is gripped by a user (a doctor, etc.). The operation part 22 also has a shape extending almost in the z direction. However, a central axis (central line) 36 of the operation part 22 is shifted toward the positive side in a y direction with respect to a central axis 32 of a shaft-like part 30 described below. The front side of the operation part 22 is a transition portion 44. The central axis 34 is inclined across the central axis 32 and the central axis 36. As a result, the main body 16 has a crank shape.

A gap 42 is formed on the upper side of a rod-like grip portion in the operation part 22. With such a configuration, the upper side of a tip part 24 is not so thickened. Therefore, the puncture needle 14 can be brought near to the main body 16.

The insertion part 20 is configured by the tip part 24 and a middle part 26 connected to the tip part 24. The tip part 24 is a head part, and is provided with the vibrator part and the scanning mechanism therein. Specifically, a medium chamber is formed in the tip part 24. In the medium chamber, the vibrator part is mechanically scanned. The tip part 24 includes a central axis 38. The central axis 38 is shifted toward the positive side in the y direction from the central axis 32 of the shaft-like part 30. The shift amount in the shift direction is indicated with Symbol 40.

The middle part 26 includes the shaft-like part 30 of a rod or cylindrical shape, and a neck part 28 which is connected to the front side thereof. The neck part 28 has a shape gradually thickening from the shaft-like part 30 to the tip part 24. The tip part 24 becomes thicker than the shaft-like part 30. The tip part 24 and the neck part 28 can be said as a thickened part 41 when viewed from the shaft-like part 30. The tip part 24 is thickened in the shift direction.

In the ultrasonic probe 10 according to the embodiment, as described below, a motor as the driving source is disposed inside a front portion 26A of the middle part 26. The driving force thus generated is transferred to the scanning mechanism, and the vibrator part is mechanically by the scanning mechanism. In addition, in the ultrasonic probe 10 according to the embodiment, as described below, a compact and light-weight structure is employed as the inner structure of the tip part 24.

Figure 2:
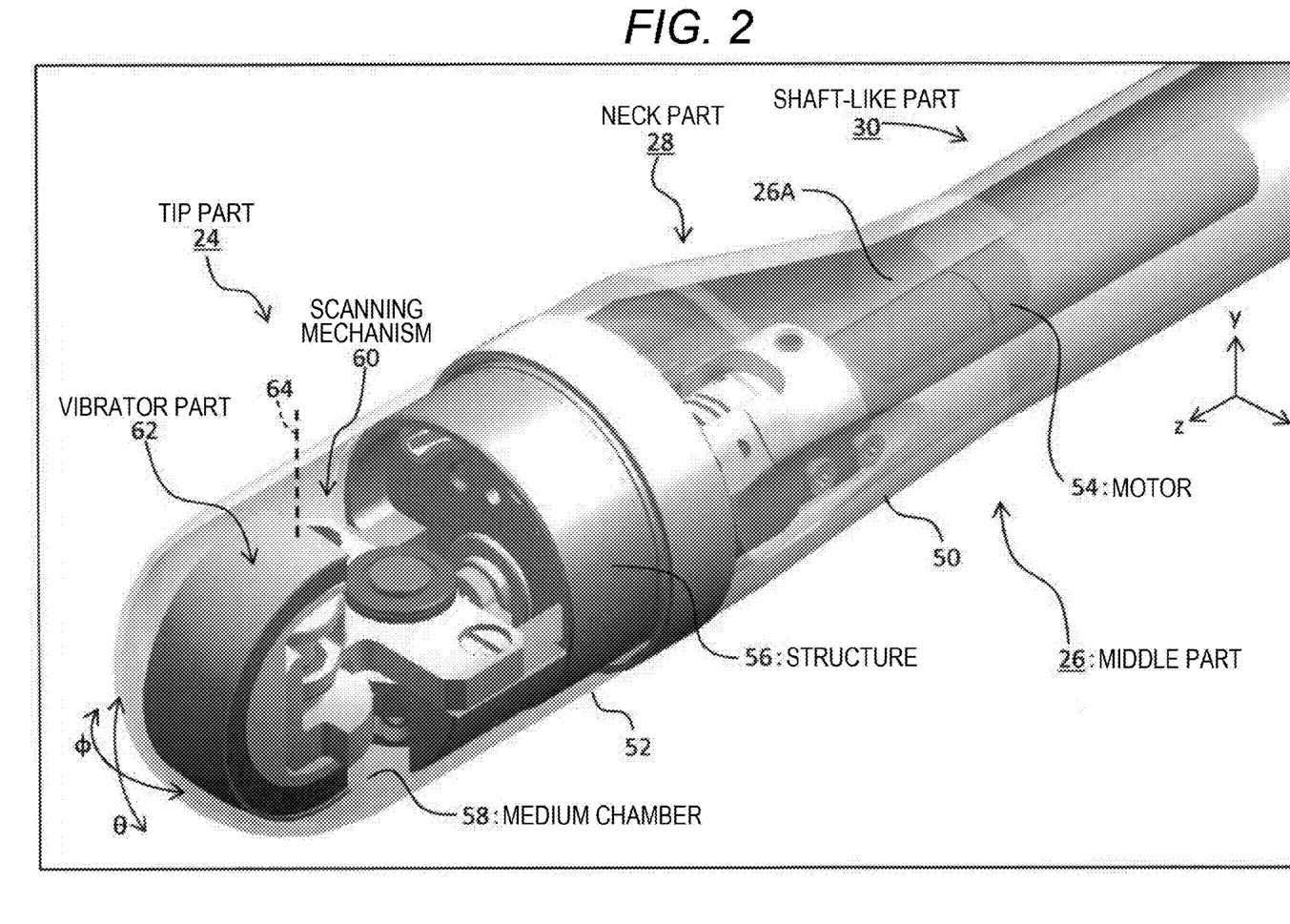
FIG. 2 is a perspective view illustrating a tip part and a neck part.

FIG. 2 illustrates the inside of the tip part 24 and the middle part 26. Further, the y direction in FIG. 1 represents the lower direction, and the y direction in FIG. 2 represents the upper direction.

The tip part 24 includes a case (tip part case) 52. A medium chamber 58 of airtightness is formed in the case 52. The medium chamber 58 is filled with a sound propagating medium such as insulating oil. In the medium chamber 58, a vibrator part 62 is mechanically scanned by a scanning mechanism 60. Specifically, the vibrator part 62 oscillates about a rotation axis (central axis) 64 of the shaft member described below. The rotation axis 64 is in parallel to the y direction.

In FIG. 2, the electronically scanning direction of an arc shape is illustrated as a θ direction, and the mechanic scanning direction of an arc shape is illustrated as a φ direction. The central point (middle point) in each scanning direction is on the central axis (see Symbol 38 in FIG. 1) of the tip part 24. The vibrator part 62 includes a vibration element array which is configured by a hundred and several tens of vibration elements paralleled in the θ direction. The vibrator part 62 mechanically scans one direction and the other direction in repetition while repeatedly performing the electronically scanning of an ultrasonic beam. With this configuration, a three-dimensional echo data capture region is repeatedly formed. In the main body of the ultrasonic diagnosis apparatus (not illustrated), an ultrasonic image is formed on the basis of volume data acquired from the three-dimensional echo data capture region.

A structure 56 which serves as a frame or a base is provided in the tip part 24. The structure 56 is configured of metal. The scanning mechanism 60 is directly held by the structure 56. In addition, the vibrator part 62 is indirectly held by the structure 56. The structure serves as a partition together with the case 52 to define the medium chamber 58.

The middle part 26 includes a case (middle part case) 50 of a cylindrical shape forming a sheath of the shaft-like part 30 and the neck part 28. Both of the case 50 and the case 52 are configured of insulating resin. At least an ultrasonic transparent portion in the case 52 is configured of a material having an acoustic impedance close to that of a living body.

As described above, a motor 54 is disposed as a driving source in the front portion in the middle part 26. The tip portion of the motor 54 is held in the cantilever system by the holding member (a holder described below) in the neck part 28. The motor 54 is disposed on the central axis (see Symbol 32 in FIG. 1) of the shaft-like part 30, and is formed in an elongating shape along the central axis. Specifically, the motor 54 is formed in a cylindrical shape. The motor 54 is, for example, a brushless motor. Other types of motors may be used. A driving source other than a motor may be used.

Figure 3:
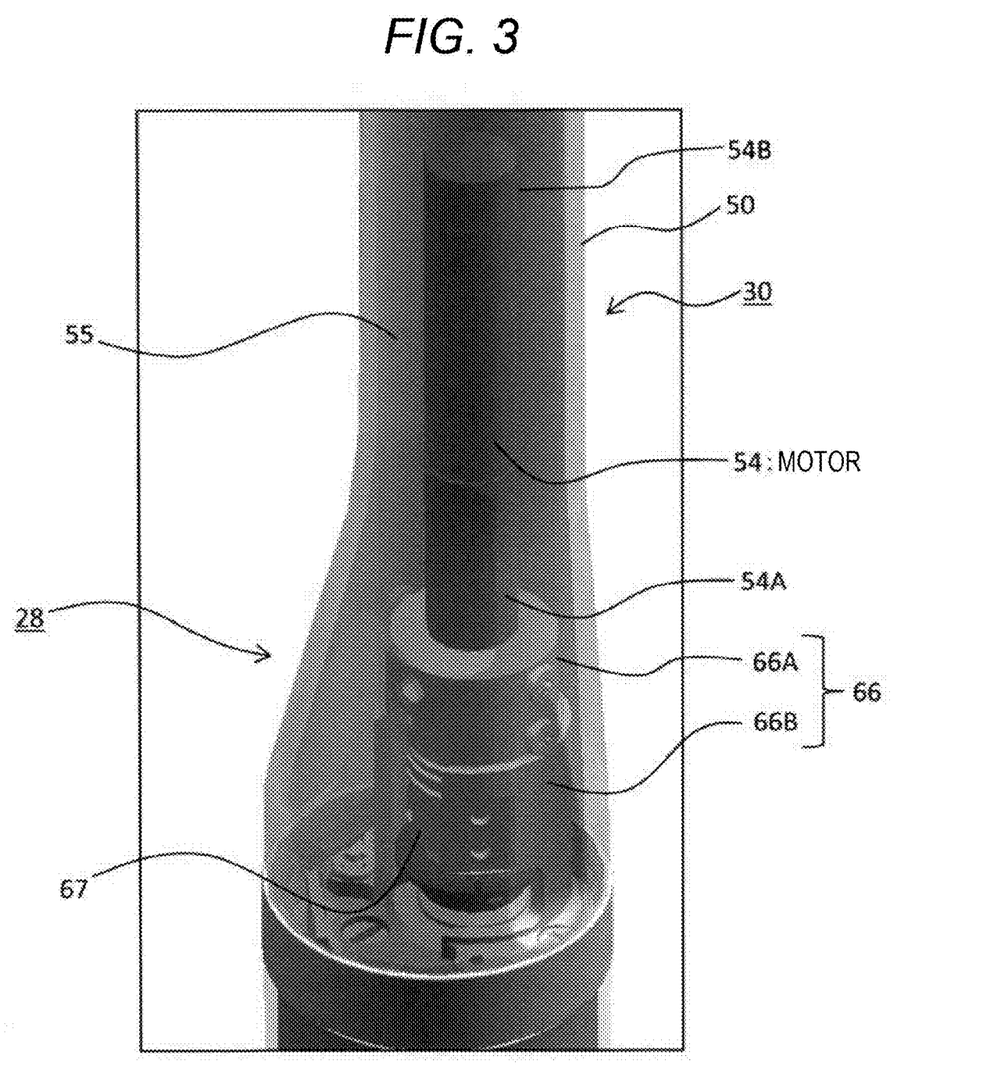
FIG. 3 is a perspective view illustrating a motor which is disposed in a middle part.

FIG. 3 is a perspective view of the middle part, and illustrates the motor 54. As described above, the middle part is configured by the shaft-like part 30 and the neck part 28. The case 50 is a hollow cylindrical member. A cylindrical holder 66 is disposed in the neck part 28. The holder 66 is configured by a first portion 66A and a second portion 66B. In the illustrated configuration, the first portion 66A holds a tip portion 54A of the motor 54. The holding system is a cantilever system, and a rear end portion 54B of the motor 54 is not held. With the cantilever system, the number of components can be reduced, and the assembly performance can be made favorably. In other words, a coupling 67 is rotatably disposed in the second portion 66B. The coupling 67 is a member which connects a motor shaft and a shaft for transferring the driving force.

The holder 66 is connected to the structure (see Symbol 56 of FIG. 2) in the tip part. At last, the structure indirectly holds the motor 54. More specifically, a ring-like gap 55 is formed between the motor 54 and a metal pipe described below around the motor 54. The wiring member passes through the gap 55. A sensor is provided to detect a rotation angle of the motor 54, but not illustrated in the drawing. The inside of the neck part 28 has space compared to the inside of the shaft-like part 30. Therefore, the holder 66 is provided to hold the tip portion of the motor 54 with respect to the inner space of the neck part 28. Moreover, the tip portion of the motor 54 may be directly held by the structure in the tip part. The empty space (the space on the left side of the holder 66 in FIG. 3) generated adjacent to the holder 66 in the neck part 28 is used as a space where the wiring member passes through.

Figure 4:
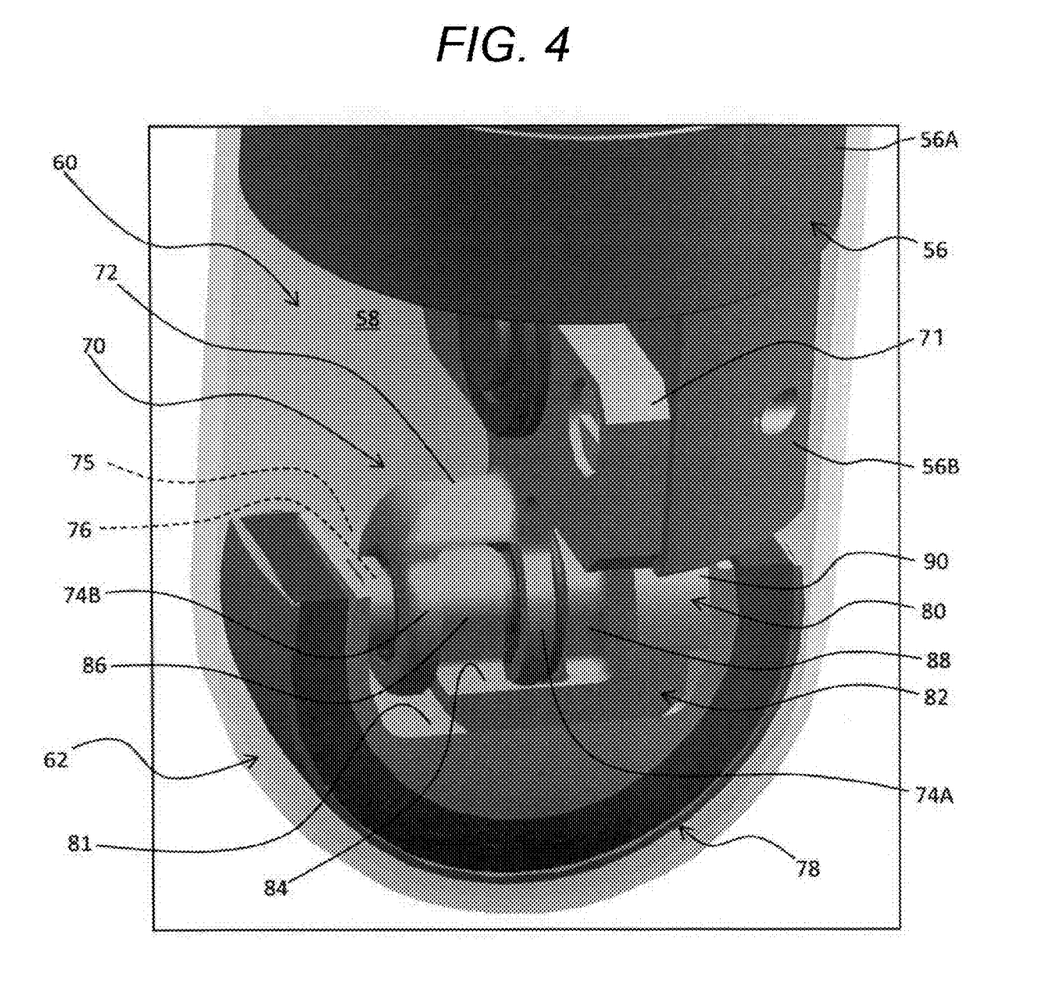
FIG. 4 is a perspective view illustrating a structure in the tip part.

FIG. 4 illustrates a structure in the tip part. The structure 56 is configured by a base part 56A as a circular pedestal and a support part 56B which forms a frame. The base part 56A and the support part 56B may be integrated. The support part 56B has a hollow structure, and stores the middle shaft member and a plurality of gears in the support part 56B. As already described, the medium chamber 58 as an airtight chamber is formed in the tip part. The scanning mechanism 60 and the vibrator part 62 as a movable body are disposed in the medium chamber 58.

The scanning mechanism 60 includes a bearing member 70, the shaft member 76, and a transfer mechanism 80. The shaft member 76 is a member for vibrating the vibrator part 62. The vibrator part 62 rotatably moves about the central axis (central line) of the shaft member 76. The transfer mechanism will be described below.

The bearing member 70 includes an attachment end 71, a middle part 72, a first bearing end (first bearing) 74A, and a second bearing end (second bearing) 74B. The attachment end 71 includes a thick plate shape. The attachment end 71 is fixed onto an attachment surface of the support part 56B. The middle part 72 connected to the attachment end 71 extends along the shaft member 76. The first bearing end 74A is connected a first position on a side near the attachment end 71 in the middle part 72. The second bearing end 74B is connected to a second position separated away from the attachment end 71 in the middle part 72. Each of the bearing ends 74A and 74B has a ring shape, and includes a bearing. The first position is a position where the central axis of the tip part passes through or a position near the central axis. On the rotation axis, the second position is set on one side of the first position, and a third position is set on the other side of the first position. A spur gear 90 described below is provided at the third position.

The middle part 72 and two bearing ends 74A and 74B all are formed in a fork shape. The shaft member 76 is rotatably held by two bearing ends 74A and 74B at two positions separated away from each other in the rotation axis. With this configuration, the holding state of the shaft member 76 is stabilized. Further, bearings or bearing ends may be provided in other device. In this embodiment, the shaft member 76 rotatably moves together with the vibrator part 62. However, it may be considered that the shaft member 76 is configured as a non-rotation axis. In the embodiment, a short shaft member 76 is used, and the center portion and one end are held instead of both ends of the shaft member 76. As a result, it becomes enabled that a member of transferring the driving force to the other end of the shaft member 76 is provided.

The vibrator part 62 includes a bent body 78 which is bent in an arc shape or a semicircular shape. The bent body 78 is also a laminated body made of a plurality of layers. The laminated structure in the bent body 78 is formed almost to the end in a bending direction (electronically scanning direction). In the embodiment, there is no structure to hold the shaft member 76 in both ends of the bent body 78.

Specifically, the bent body 78 includes a vibration element array which is configured by a plurality of vibration elements arranged in the electronically scanning direction of an arc shape. In the bent body 78, one or a plurality of alignment layers are provided on the front side (on an ultrasonic emission side) of the vibration element array, and the acoustic lens is provided on the front side of one or the plurality of alignment layers. The surface of the acoustic lens faces the inner surface of the tip part case. In the bent body 78, a backing is provided on the rear side, that is, the rear surface side of the vibration element array (on a side opposite the ultrasonic emission side). The backing is configured by a material which absorbs or disperses unnecessary ultrasonic waves.

The bent body 78 is attached to a movable base 81 which serves as a pedestal or a frame. The movable base 81 is configured by a metallic material such as aluminum. The movable base 81 is configured by a center portion and a pair of blade portions. The center portion is formed in a shape such as the bottom of a ship. The pair of blade portions is bent and extends from both ends of the center portion. The movable base 81 includes a cylindrical front surface bonded to the back surface (rear surface) of the backing, and a flat attachment surface to which a movable frame 82 is attached. With the attachment surface, the movable frame 82 is easily attached to the movable base 81, and fixedly attached.

The movable frame 82 is a coupling member to attach the vibrator part 62 to the shaft member 76. Specifically, the movable frame is configured by a metallic material such as aluminum. The movable frame 82 includes a pair of fixing parts 86 and 88 which is fixed thereto while holding the rotation axis. In addition, the movable frame 82 includes the spur gear 90 which forms a part of the transfer mechanism 80. The spur gear 90 is a driven gear. In view of the above function of the movable frame 82, the movable frame 82 is naturally considered as a member belonging to the scanning mechanism 60.

On the rear surface side of the vibrator part 62, a concave part 75 is formed as an inner space configured inside the movable base 81. The concave part 75 has a rectangular shape when viewed roughly. The concave part 75 includes a rear surface opening and two side surface openings. In the concave part 75, at least a portion of the scanning mechanism 60 is inserted. In the embodiment, the entire shaft member 76 in the scanning mechanism 60 is inserted. Further, only a portion of the shaft member 76 may be inserted in the concave part 75. In the embodiment, the main parts of the first bearing end 74A, the second bearing end 74B, and the movable frame 82 are also disposed in the concave part 75. Further, these portions may protrude from the concave part 75. By the way, even if the movable frame 82 is regarded as a portion of the vibrator part 62, a portion of the scanning mechanism is inserted to the concave part as a hollow part opened on the rear surface side.

A semi-cylindrical shape (without the concave part) may be employed as the vibrator part 62. In this case, there is caused a portion which does not actually serve on the rear side of the semi-cylindrical portion. In the embodiment, the concave part 75 is formed in all or a part of the portion.

According to the embodiment, the concave part 75 is formed in the vibrator part 62, so that the vibrator part 62 is reduced in weight as much as the concave part. In addition, the resistance of the vibrator part 62 received from the sound propagating medium is reduced. In addition, according to the embodiment, the shaft member 76 is provided in the concave part 75. Therefore, the shaft member 76 is brought near to the vibrator part 62. With this configuration, the inner structure of the tip part can be made compact. In addition, the number of members for connecting the shaft member 76 and the vibrator part 62 can be reduced. Therefore, the weight can be reduced as much as the reduced members. At the same time, the resistance of the movable body received from the sound propagating medium can be reduced. As a result, it is possible to reduce the tip part in size and in weight. Further, the resistance generated in the vibrator part 62 and the scanning mechanism 60 is reduced. The driving force required for the mechanical scanning can be reduced. That is, the motor can be made compact. In other words, the motor can be disposed in the middle part without thickening the middle part.

Figure 5:
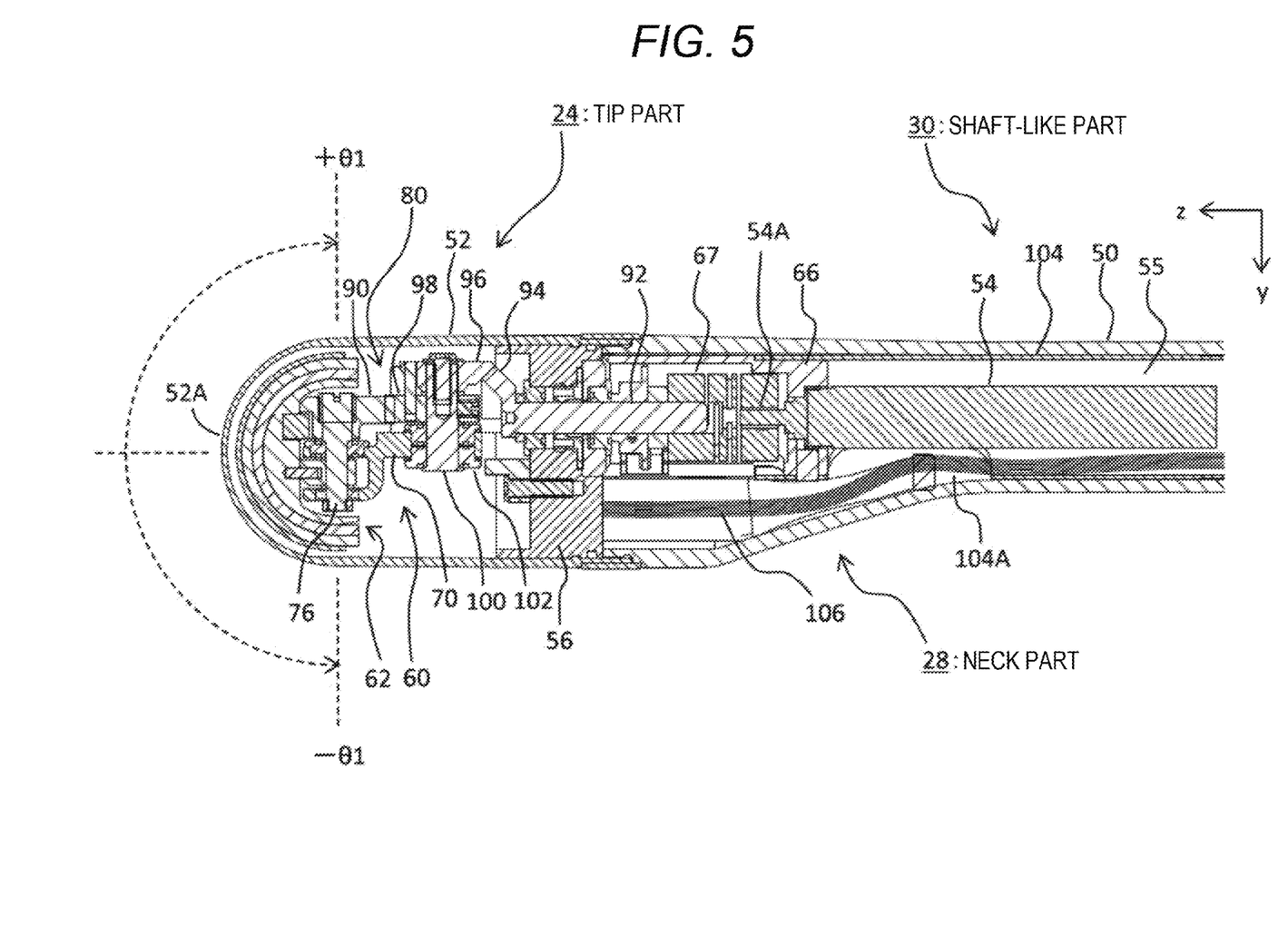
FIG. 5 is a cross-sectional view illustrating a yz cross section of the ultrasonic probe according to the embodiment.
Figure 6:
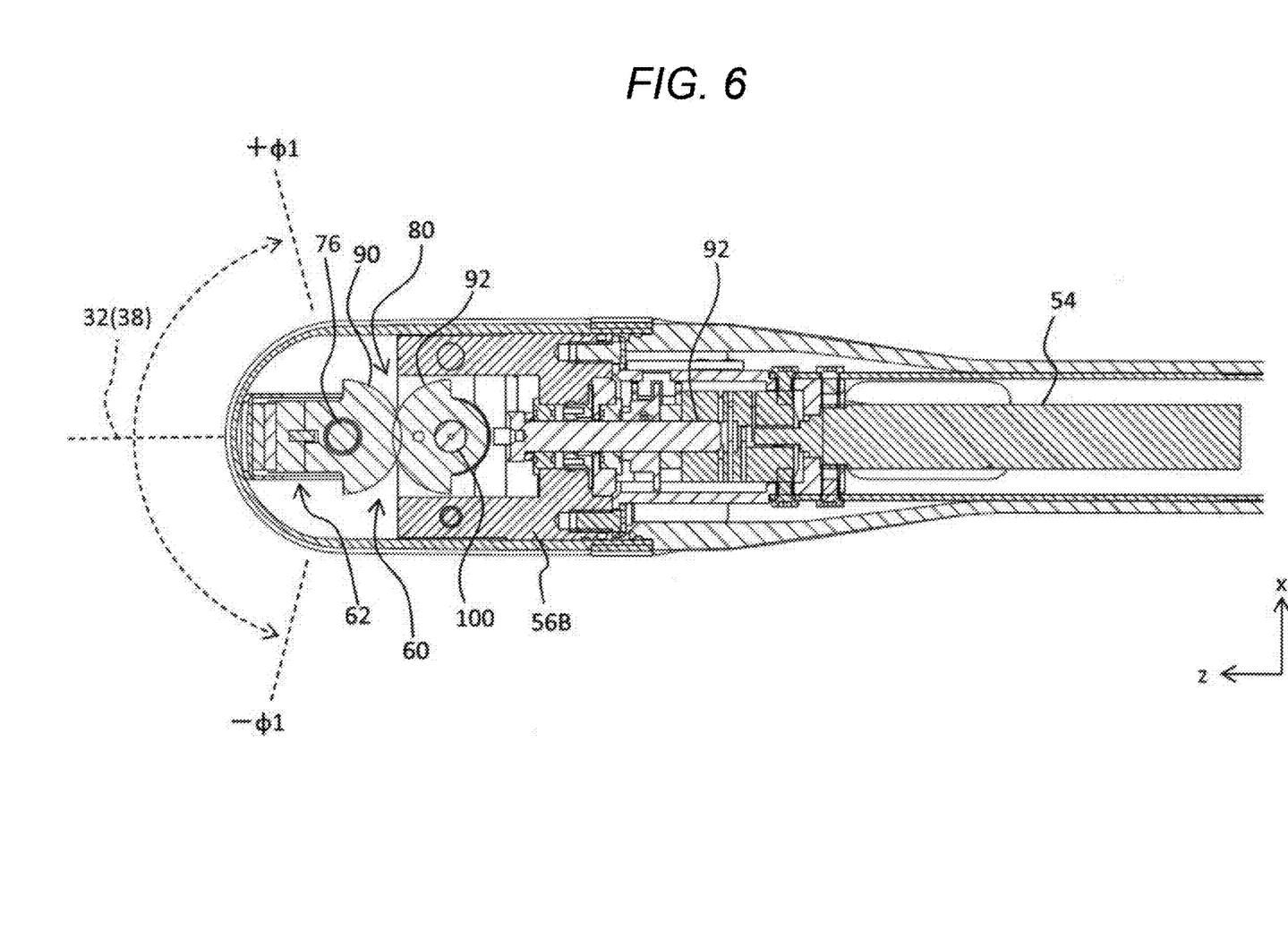
FIG. 6 is a cross-sectional view illustrating an xz cross section of the ultrasonic probe according to the embodiment.

The detailed structure of the tip part 24, the neck part 28, and the shaft-like part 30 will be described using FIGS. 5 and 6. FIG. 5 illustrates a yz cross section, and FIG. 6 illustrates an xz cross section.

In FIG. 5, the motor 54 is disposed along the neck part 28 and the shaft-like part 30 (in the front portion in the middle part). In the middle part, a pipe 104 made of a hard material (specifically, metal) is disposed in the hollow case 50 made of an insulating material. The pipe 104 serves as an outer frame, that is, increasing the strength of the insertion part. Simultaneously, an electromagnetic shield operation is achieved. The outer surface of the pipe 104 comes into tight contact with the inner surface of the case 50. The pipe 104 is configured of metal such as stainless steel. The tip portion of the pipe 104 is connected to the holder 66 which holds the tip portion of the motor 54. An opening 104A of a slit shape is formed in the side surface of the tip portion of the pipe 104. A wiring member 106 enters the pipe 104 through the opening 104A. The ring-like gap 55 is generated between the pipe 104 and the motor 54, and the wiring member 106 passes through the gap 55. The wiring member 106 is configured as a laminated body (sheet bundle) made of a plurality of sheets, and the wiring member 106 passes through the gap 55 in this sheet bundle state. Further, a plurality of dispersed sheets may pass through the gap 55. Further, in FIG. 5, the wiring member outputting from the vibrator part 62 is not illustrated in the tip part 24.

The shaft of the motor 54 is connected to a shaft 92 by the coupling 67. The motor 54 and the shaft 92 are disposed in parallel on the central axis of the shaft-like part 30. A bevel gear 94 is formed in the tip portion of the shaft 92. On the other hand, a bevel gear 96 is provided in the middle shaft member 100 which is rotatably provided. The bevel gear 94 and the bevel gear 96 are meshed. The latter is driven according to the driving rotation of the former. The middle shaft member 100 is rotatably held by a pair of bearings 102. The pair of bearings 102 and the bearing member 70 described above are held by the structure 56.

A spur gear 98 is fixed to the middle shaft member 100. The spur gear 98 is meshed with the spur gear 90 on a side near the vibrator part 62. The spur gear 90 is driven by the rotation of the spur gear 98. With this configuration, the vibrator part 62 rotatably moves about the rotation axis (central axis) of the shaft member 76. Specifically, if the motor 54 rotates in one direction, the vibrator part 62 vibrates toward one side in the mechanically scanning direction. If the motor 54 rotates in the other direction, the vibrator part 62 vibrates to the other direction of the mechanically scanning direction.

The scanning mechanism 60 includes the transfer mechanism 80. The transfer mechanism 80 in the embodiment includes the shaft 92, the bevel gear 94 as the end of the shaft 92, the middle shaft member 100, the spur gear 98, and the spur gear 90. In the scanning mechanism 60, the bearing member 70 and the shaft member 76 are included besides the transfer mechanism 80. Further, the illustrated specific configurations are given as merely exemplary. Except the middle shaft member, the rotation force of the shaft 92 may be directly transferred to the vibrator part 62. The rotation speed may be adjusted by an operation of a plurality of gears. Further, a portion of the shaft exists in the neck part 28, but the main portion of the scanning mechanism 60 is disposed in the tip part 24. Therefore, the scanning mechanism 60 can be said as a mechanism disposed in the tip part 24. Further, the shaft 92 may be considered as an element other than the scanning mechanism 60.

In FIG. 5, one end of the electronically scanning direction is expressed as+θ1, and the other end of the electronically scanning direction is expressed as−←1. An angle range of the electronically scanning may be a range from−90° to+90°. Further, the central point (and the original point) of the electronically scanning direction is located on the central axis 38 of the tip part 24. The case 52 is connected to the case 50. A semi-circle portion in the case 52 is a living-body contact portion 52A.

In FIG. 6, the motor 54 and the shaft 92 are disposed on the central axis 32 of the shaft-like part. The middle shaft member 100 is rotatably held by a pair of bearing s which are fixed to the support part 56B. The spur gear 98 is fixed to the middle shaft member 100, and is meshed with the spur gear 90 on a side near the vibrator part 62. These components form a part of the transfer mechanism 80. In FIG. 6, one end in the mechanically scanning direction is expressed as+φ1, and the other end in the mechanically scanning direction is expressed by−φ1. An angle range of the mechanical scanning may be a range from−75° to+75°. Further, the central point (and the original point) of the mechanically scanning direction is located on the central axis 38 of the tip part 24.

Figure 7:
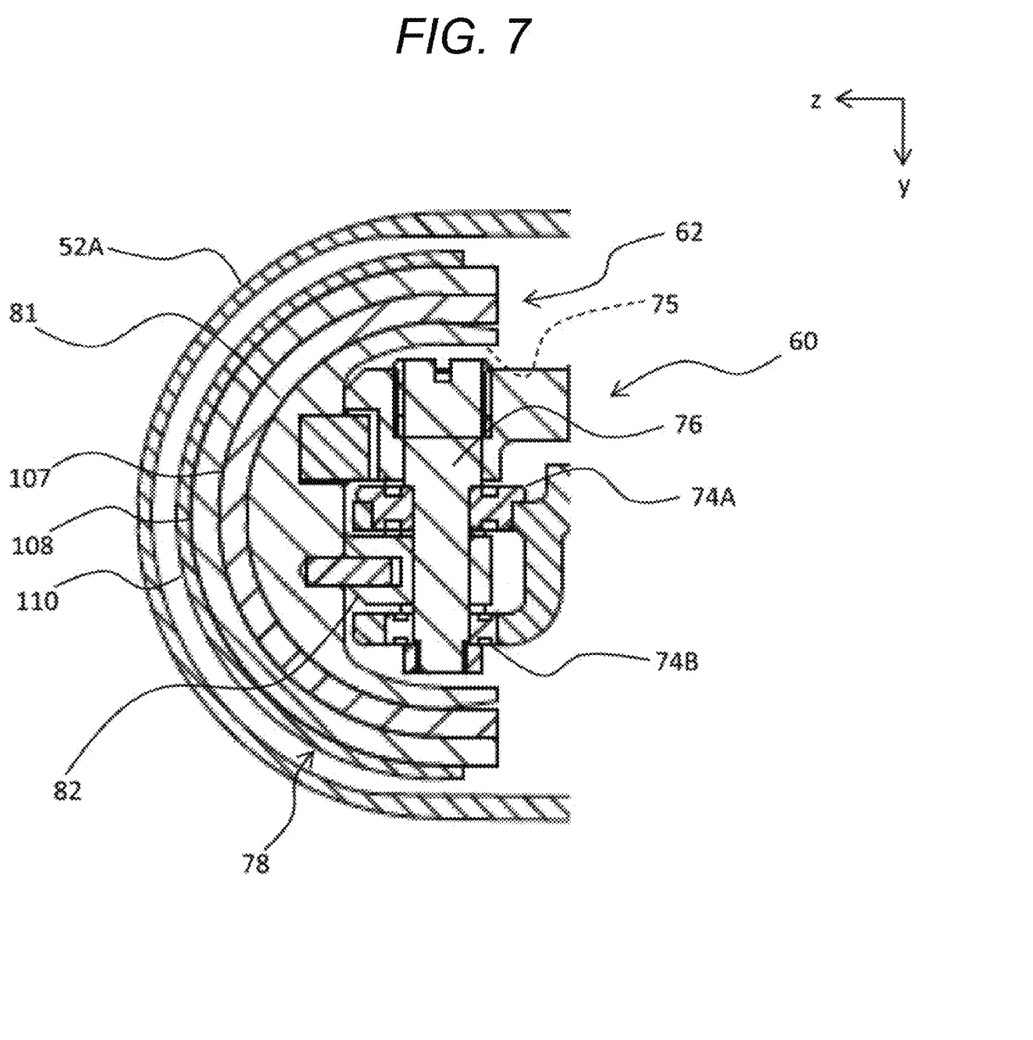
FIG. 7 is a cross-sectional view illustrating a vibrator part and a part of a scanning mechanism on an enlarged scale.

FIG. 7 illustrates a partially enlarged cross-sectional view of the tip part. The scanning mechanism 60 includes the shaft member 76. The shaft member 76 is rotatably held by the first and second bearing ends 74A and 74B. On the other hand, the vibrator part 62 includes the bent body 78 and the movable base 81. A bent portion indicated by Symbol 108 corresponds to the vibration element array and one or a plurality of alignment layers. An acoustic lens 110 is provided on the front side of the portion 108. The backing 107 is provided on the rear side of the portion 108, that is, on the rear surface side. The bent body 78 is fixed to the movable base 81. The concave part 75 is formed on the inner side of the movable base 81. In the embodiment, the entire shaft member 76 is stored in the concave part 75, and the main portion of the first and second bearing ends 74A and 74B is stored. Further, the movable frame 82 forming a part of the scanning mechanism 60 is stored.

With such a configuration, the tip part can be reduced in size and weight. In addition, a load caused at the time of vibration of the vibrator part 62 is reduced, so that the motor as the driving source is reduced in size. At least a part in the shaft member enters the concave part 75, so that the above merits are achieved.

Figure 8:
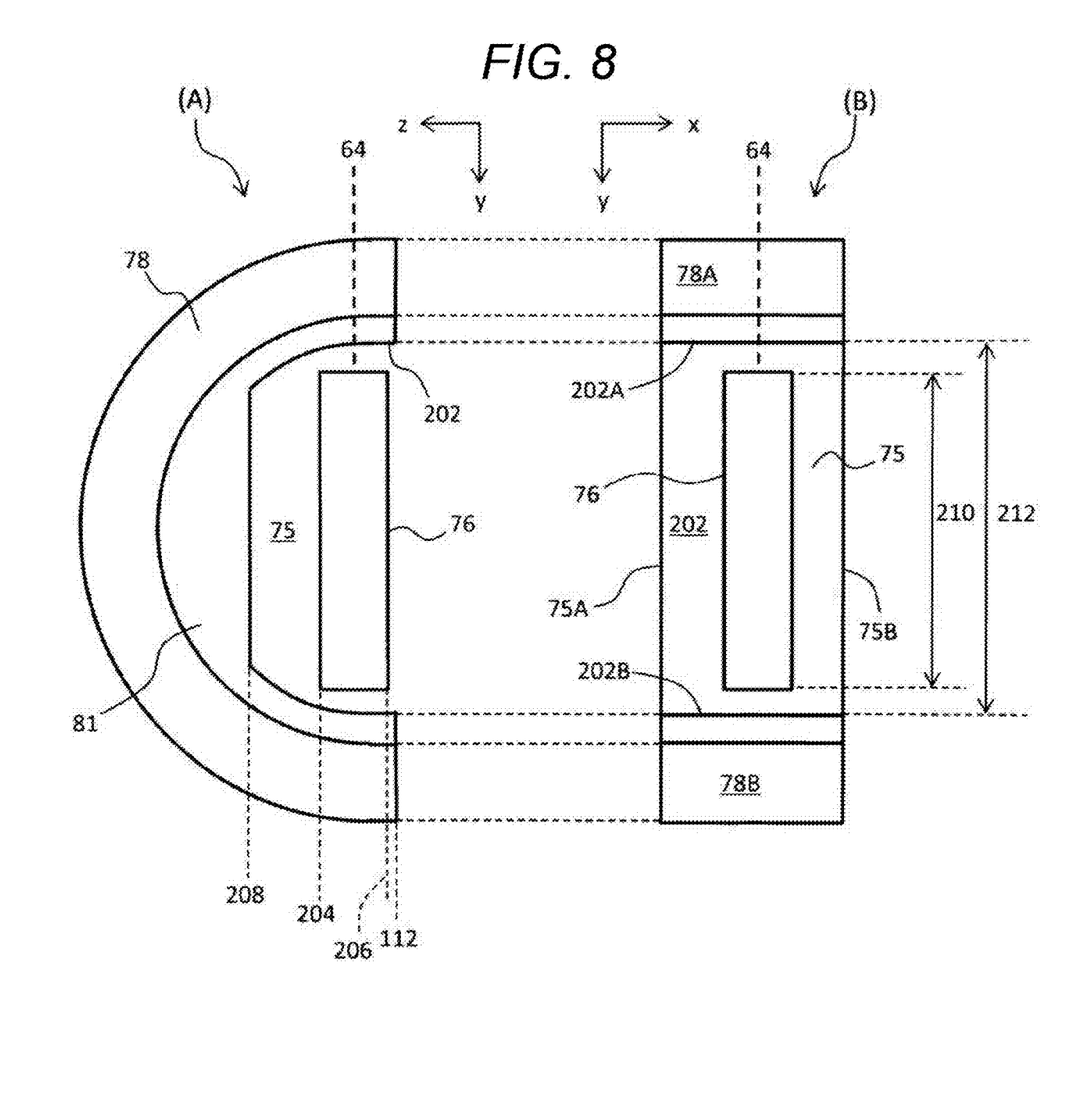
FIG. 8 is a schematic view illustrating the vibrator part and the shaft member.

FIG. 8 illustrates a schematic view of the tip part. (A) illustrates a yz plane, and (B) illustrates an xy plane. In a case where the concave part 75 is regarded as a wide groove, the y direction represents a groove width direction, the x direction represents a groove central line direction, and the z direction represents a groove depth direction. In the concave part 75, the y direction represents a longitudinal direction, and the x direction represents a lateral direction. Symbol 64 indicates the central axis of the shaft member 76, that is, the rotation axis.

In the yz plane illustrated in (A), the movable base 81 is provided on the rear surface side of the bent body 78. An inside space on the rear surface side of the movable base 81 is the concave part 75. The concave part includes a rectangular rear surface opening 202, and the position in the z direction is indicated with Symbol 112. The positions of the both ends of the shaft member 76 in the z direction are indicated with Symbols 204 and 206. The bottom position of the concave part in the z direction is indicated with Symbol 208. The positions 204 and 206 of the both ends of the shaft member in the z direction are located on the front side (the front side in the z direction) from the position 112 of the rear surface opening 202. In other words, the entire shaft member 76 in the yz plane is stored in the concave part 75.

In the xy plane illustrated in (B), a portion between one end 78A and another end 78B in the electronically scanning direction in the bent body 78 corresponds to the rear surface opening 202 of the concave part 75. The rear surface opening 202 includes one edge 202A abutting on the end 78A and another edge 202B abutting on the other end 78B. A portion between the edge 202A and the other edge 202B corresponds to an opening length 212. An entire length 210 in the y direction of the shaft member is shorter than the opening length 212. In other words, the entire shaft member 76 is stored in the concave part 75 even in the xy plane. Both ends of the shaft member 76 are in a non-contact state with the bent body 78. In other words, a short shaft member 76 is used in the embodiment.

The concave part 75 includes the rear surface opening 202 and a pair of side surface openings 75A and 75B. The area of a portion to come in conflict with the sound propagating medium in the vibrator part by the pair of side surface openings 75A and 75B. Further, a pair of side surface openings 75A and, 75B is configured to be closed. For example, a swollen portion of a streamlined shape may be provided with respect to the vibrator part.

The thickness of the center portion of the movable base 81 may be made thin, so that the depth of the concave part 75 may be made deep. In a case where the total length of the bent body 78 in the electronically scanning direction is short, only a part of the shaft member 76 may be inserted in the concave part 75. The shaft member may be disposed to connect the end 78A and the other end 78B in the bent body 78. In that case, the shaft member may be held between the end 78A and the other end 78B. It is hard that a bearing structure is provided on the outer side of the bent body in order to reduce the tip part inserted in the body cavity in size. Therefore, instead of the both ends of the shaft member, a configuration for holding the shaft member is desirably employed in the middle part except the both ends. As a modification, a portion of the configuration (for example, a plurality of bearings) of the shaft member may be inserted to the concave part.

Figure 9:
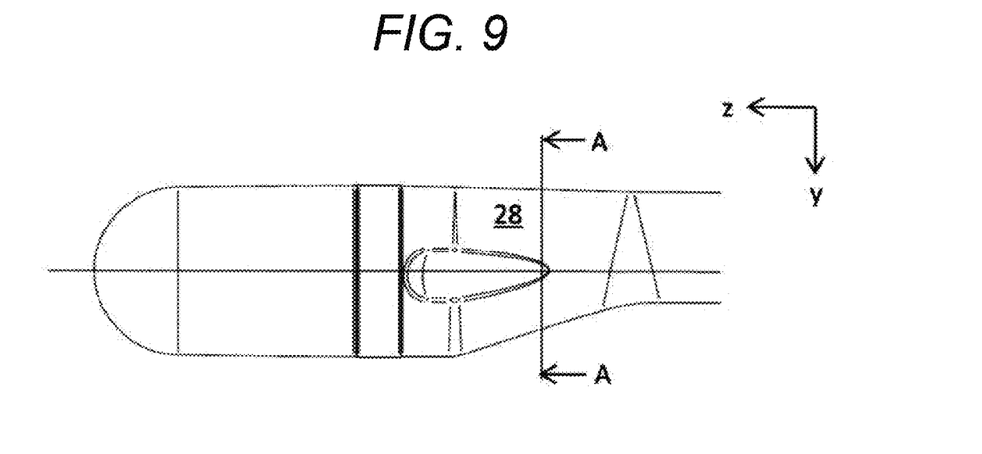
FIG. 9 is a side view illustrating a cross-sectional position.
Figure 10:
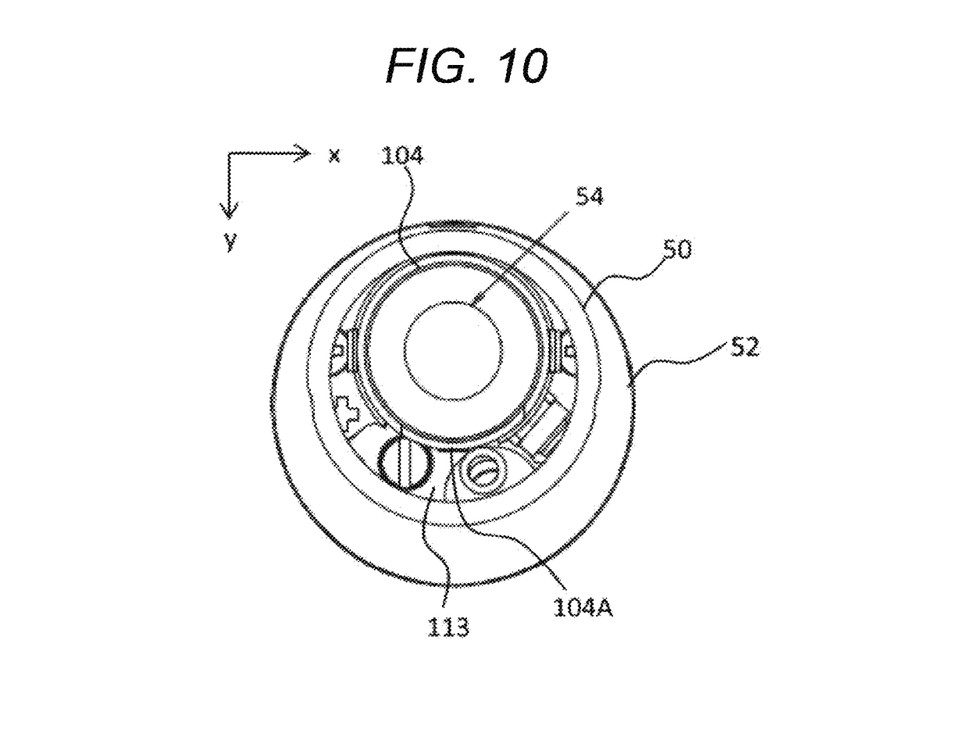
FIG. 10 is a cross-sectional view corresponding to the cross-sectional position illustrated in FIG. 9.

FIG. 9 illustrates a cross-sectional position taken along line A-A in the neck part 28. The cross-sectional view corresponding to the position is illustrated in FIG. 10. In FIG. 10, the case 50 of the middle part and the case 52 of the tip part are illustrated. The motor 54 is disposed in the pipe 104. The opening 104A is formed on the lower side (the positive side in the y direction) in the pipe 104. The wiring member (not illustrated) is inserted into the pipe 104 from a space 113 in the neck part to the opening 104A.

Figure 11:
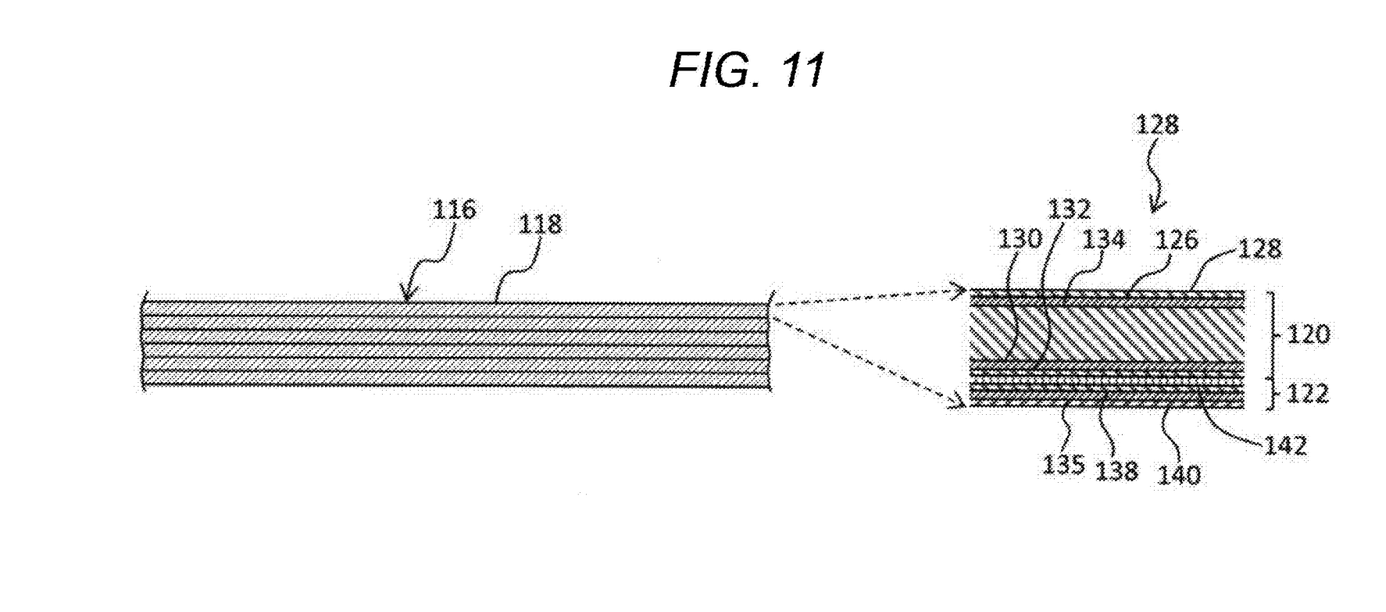
FIG. 11 is a diagram illustrating a wiring sheet bundle.

FIG. 11 illustrates the wiring member. A wiring member 116 described in the drawing is configured by the plurality of stacked wiring sheets 118, and forms a sheet bundle. The plurality of wiring sheets 118 are drawn out of the side surface on one side of the vibrator part, and appropriately folded to form the sheet bundle. The sheet bundle passes through the structure (partition) from the medium chamber and is inserted to the inner space of the neck part, and passes through the inner space of the pipe and is drawn out up to the operation part.

In each sheet 118, at least a portion near the motor is schematically illustrated on the right side of FIG. 11. The sheet 118 is configured by the wiring sheet 120 and a ground tape 122. The wiring sheet 120 includes a sheet body 134 made of an insulating material in the example of the drawing, and a ground layer 126 and an insulating layer (coating layer) 128 are formed as a surface electrode in one side thereof. On the other side of the sheet body 134, a signal line array 130 and an insulating layer 132 are formed as a wiring pattern. The ground tape 122 includes an adhesive layer 142, an insulating layer 138, and a ground layer 135 and an insulating layer 140 as a surface electrode over a side near the wiring sheet 120 to a side away therefrom.

Since the signal line array 130 is interposed by a pair of ground layers 126 and 135, it is effectively suppressed that the electromagnetic noises enter the signal line array 130. In particular, in a case where the motor acts as a noise source, the configuration illustrated in FIG. 11 is desirably employed. In the tip part, each sheet is desirably configured in each wiring sheet 120. With such a configuration, it is possible to reduce the load generated at the time of mechanic scanning of the vibrator part.

According to the embodiment, since the concave part is formed in the vibrator part, the vibrator part can be reduced in weight, and the load generated when the vibrator part comes into conflict with the sound propagating medium can be reduced. With the shaft member for the vibrating shaft member of the vibrator part which is disposed in the concave part, the vibrator part and the shaft member can come into contact with each other, and the scanning mechanism can be made simplified and reduced in weight. In addition, it is possible to reduce the load generated when the scanning mechanism comes into conflict with the sound propagating medium. Therefore, the tip part can be reduced in size and in weight. In addition, a small motor can be employed as the driving source. As a result, the motor can be disposed inside the middle part. This configuration has a merit on reducing the ultrasonic probe still more in weight. In addition, it is possible to shape the operation part to some degree of freedom.

The above configuration may be applied to a body cavity insertion type such as a transvaginal probe, a transrectal probe, and a transesophageal probe. Further, the inner structure of the tip part may be applied to a body surface contacting type probe besides the body cavity insertion type probe.

The invention claimed is:

1. An ultrasonic probe, comprising:
   a tip part configured to be inserted in a body cavity, and to store a vibrator part and a scanning mechanism, the scanning mechanism configured to mechanically scan the vibrator part;
   an operation part configured to be gripped by a user; and
   a middle part disposed between the tip part and the operation part, and storing a driving source configured to generate a driving force to be transferred to the scanning mechanism,
   wherein the middle part includes a neck part and a front portion which is connected to the tip part, and the driving source is disposed in the front portion,
   wherein a tip portion of the driving source is held in a cantilever system by a holding member which is disposed in the tip part or in the middle part,
   wherein the tip part includes a partition defining a medium chamber of the tip part,
   wherein the scanning mechanism includes a transfer structure including a shaft extending from the neck part and through the partition,
   wherein the driving source is configured to provide a rotational force to the shaft to directly transfer the rotational force to the vibrator part,
   wherein the ultrasound probe comprises a first central axis and a second central axis, and wherein the tip part includes the second central axis which is in parallel with the first central axis and is provided at a position shifted from the first central axis, and wherein a central point of an electronically scanning direction and a central point of a mechanically scanning direction are on the second central axis.

2. The ultrasonic probe according to claim 1,
   wherein the middle part includes:
   a hollow resin case, and
   a metal pipe disposed in the resin case and connected to the holding member while storing the driving source.

3. The ultrasonic probe according to claim 1, wherein the middle part includes a shaft-like part and wherein the neck part is connected to the shaft-like part, wherein the tip part is thicker than the shaft-like part, wherein the neck part is gradually thickened from the shaft-like part to the tip part, and wherein the holding member is disposed in the neck part.

4. The ultrasonic probe according to claim 3, wherein the shaft-like part includes the first central axis, wherein the driving source is disposed on the first central axis in the middle part, and wherein the driving source extends along the first central axis.

5. The ultrasonic probe according to claim 1,
   wherein the middle part includes a ring-like gap generated about the driving source, and
   wherein a wiring member output from the vibrator part passes through the ring-like gap and extends up to the operation part.

6. The ultrasonic probe according to claim 5,
   wherein the wiring member includes at least one wiring sheet which includes a signal line array,
   wherein the wiring sheet includes a driving source proximity portion having a portion passing through the ring-like gap,
   wherein at least the driving source proximity portion in the wiring sheet includes a first ground surface electrode provided on one side of the signal line array and a second ground surface electrode provided on another side of the signal line array.

* * * * *